United States Patent
Mueller et al.

[11] Patent Number: 6,162,214
[45] Date of Patent: Dec. 19, 2000

[54] CORNING DEVICE FOR MYOCARDIAL REVASCULARIZATION

[75] Inventors: Richard L. Mueller, Byron; Alexander Khairkhahan, Palo Alto, both of Calif.

[73] Assignee: Eclipse Surgical Technologies, Inc., Sunnyvale, Calif.

[21] Appl. No.: 09/183,757

[22] Filed: Oct. 30, 1998

Related U.S. Application Data

[60] Provisional application No. 60/064,277, Oct. 30, 1997.

[51] Int. Cl.[7] ............................................. A61B 18/18
[52] U.S. Cl. ........................... 606/15; 606/13; 606/16; 606/167; 606/170
[58] Field of Search .................. 606/170, 2, 5, 606/7–15, 89, 45, 28, 180; 600/564–568

[56] References Cited

U.S. PATENT DOCUMENTS

| | | |
|---|---|---|
| 3,913,566 | 10/1975 | Lacey . |
| 4,461,305 | 7/1984 | Cibley . |
| 4,576,162 | 3/1986 | McCorkle . |
| 4,658,817 | 4/1987 | Hardy . |
| 4,850,354 | 7/1989 | McGurk-Burleson et al. . |
| 5,263,959 | 11/1993 | Fischell . |
| 5,342,358 | 8/1994 | Daikuzono ................................ 606/45 |
| 5,358,472 | 10/1994 | Vance et al. . |
| 5,366,468 | 11/1994 | Fucci et al. . |
| 5,380,316 | 1/1995 | Aita et al. . |
| 5,403,311 | 4/1995 | Abele et al. . |
| 5,477,862 | 12/1995 | Haaga . |
| 5,496,307 | 3/1996 | Daikuzono ................................ 606/15 |
| 5,554,152 | 9/1996 | Aita et al. . |
| 5,591,159 | 1/1997 | Taheri . |
| 5,632,755 | 5/1997 | Nordgren et al. . |
| 5,658,272 | 8/1997 | Hasson . |
| 5,702,412 | 12/1997 | Popov et al. . |
| 5,728,091 | 3/1998 | Payne et al. ............................... 606/15 |
| 5,738,680 | 4/1998 | Mueller et al. ........................... 606/15 |
| 5,741,287 | 4/1998 | Alden et al. . |
| 5,766,164 | 6/1998 | Mueller et al. ........................... 606/15 |
| 5,782,823 | 6/1998 | Mueller ...................................... 606/7 |
| 5,794,626 | 8/1998 | Kieturakis . |
| 5,807,277 | 9/1998 | Swaim . |
| 5,871,495 | 2/1999 | Mueller . |
| 5,873,886 | 2/1999 | Larsen et al. ............................ 606/180 |
| 5,876,373 | 3/1999 | Giba et al. . |
| 5,899,915 | 5/1999 | Saadat . |
| 5,913,853 | 6/1999 | Loeb et al. ............................... 606/15 |
| 5,964,757 | 10/1999 | Ponzi ........................................ 606/45 |
| 5,976,164 | 11/1999 | Bencini et al. .......................... 606/170 |
| 5,984,939 | 11/1999 | Yoon ....................................... 606/170 |

FOREIGN PATENT DOCUMENTS

| | | |
|---|---|---|
| 0 807 417 A2 | 11/1997 | European Pat. Off. . |
| WO 96/35469 | 11/1996 | WIPO . |
| WO 98/19614 | 5/1998 | WIPO . |
| WO 98/24373 | 6/1998 | WIPO . |
| WO 98/25533 | 6/1998 | WIPO . |
| WO 98/39038 | 9/1998 | WIPO . |
| WO 99/20187 | 4/1999 | WIPO . |

*Primary Examiner*—John P. Leubecker
*Assistant Examiner*—Ahmed Farah
*Attorney, Agent, or Firm*—Ilene Lapidus Janofsky

[57] ABSTRACT

Apparatus and method for creating pathways in tissue and destroying the cored tissue to avoid release of the cored tissue within the body. The apparatus has a coring mechanism and a tissue vaporization mechanism. The apparatus is useful in creating revascularization pathways in the myocardium. The apparatus and methods are adaptable for either surgical or percutaneous procedures.

57 Claims, 9 Drawing Sheets

CORING DEVICE FOR MYOCARDIAL REVASCULARIZATION

PRIORITY CLAIM

This Application claims the benefit of domestic priority under 35 U.S.C. section 119(e) from U.S. Provisional Application Ser. No. 60/064,277 filed Oct. 30, 1997 entitled Coring Device for Myocardial Revascularization, which is herein incorporated by reference in its entirety.

RELATED APPLICATIONS

This application represents new embodiments to U.S. patent application Ser. No. 08/908,816, filed on Aug. 8, 1997, and issued on Nov. 2, 1999 as U.S. Pat. No. 5,976,164 entitled Method & Apparatus for Myocardial Revascularization and/or Biopsy of the Heart, which is hereby incorporated by reference.

FIELD OF INVENTION

This invention relates to the field of mechanical/laser tools for cardiac surgery, and more particularly to methods and devices for myocardial revascularization.

BACKGROUND OF INVENTION

Heart disease is a significant health problem which has been the subject of substantial medical study. Bypass surgery has become commonplace; yet such surgery may be unavailable to many patients, either because of the nature of the occlusions or the physical condition of the patient.

One promising alternative technique for treating such cases is known as transmyocardial revascularization (TMR). Although this technique was considered as early as the work of Dr. C. Beck "the Development of a New Blood Supply to the Heart By Operation," *Annals of Surgery,* Vol. 102, No. 5 (11/35) pp. 801–813, the method was not extensively studied until the work of Dr. M. Mirhoseini and M. Cayton, an example of which is found in "Lasers in Cardiothoracic Surgery" in *Lasers in General Surgery* (Williams and Williams; 1989) pp. 216–223.

Myocardial revascularization systems, used by cardiothoracic surgeons and interventional cardiologists, include a) external- to-the-heart based systems that use either a TMR surgical hand-held instrument or a minimally invasive surgical (MIS)-TMR, both of which create channels from outside the heart into the left ventricle and b) a percutaneous transluminal myocardial revascularization (PTMR) instrument that is a catheter and tissue removal energy delivery system that creates channels partially into the myocardium from inside the left ventricle. In the MIS-TMR procedure, a cardiothoracic surgeon performs a thoracotomy by incision through the chest wall to access the heart using the modified endoscopic surgical instrument containing an internal optical fiber that applies laser energy to the external portions of the heart to create channels through to the left ventricle. In the PTMR procedure, an interventional cardiologist performs a cardiac catheterization procedure using a catheter with an internal optical fiber that is inserted into the femoral artery at the groin and advanced through the heart's aorta arch into the left ventricle. Once in the ventricle, the catheter is guided to the endocardium where the device creates pathways through the endocardium and partially into the myocardium.

TMR, MIS-TMR & PTMR generally require that a physician use a hand-held device that encompasses and guides either a mechanical cutting device or one or more optical fibers through which laser energy is directed. Mechanical or laser energy cuts or vaporizes heart muscle tissue immediately in front of the distal end of the device. From the standpoint of safety and efficacy, the laser TMR procedure minimizes both ancillary tissue damage and embolic material production, both results are highly desirable. Varying penetration depths are possible.

Clinical tests have demonstrated that revascularization channels/pathways, which generally communicate with the ventricle, facilitate revascularization of the heart muscle and recovery of heart function. Recent studies further demonstrate that beneficial revascularization also occurs following creation of channels that do not remain patent and channels that do not communicate with the ventricular chamber. For example, a laser device to perform TMR is described in U.S. Pat. No. 5,380,316 which teaches of a way to form numerous channels through the heart's epicardium through to the heart's ventricle through the myocardium by a laser apparatus. Other patents describing surgical TMR include U.S. Pat. Nos. 4,658,817 and 5,554,152. Lasing through the epicardium or endocardium, as described in many laser TMR procedures, may result in some destruction of viable vascular tissue contiguous to the epicardium or endocardium. Lasing may also produce collateral tissue damage if not carefully controlled.

An alternative to use of lasers in instruments to effectuate revascularization of the heart are mechanical cutter devices to produce these channels. Early prior art methods of mechanical piercing and cutting of the heart wall were not pursued further because mechanical cutting did not produce patent channels.

A recent laser TMR device to perform transmyocardial revascularization includes some non-laser mechanisms and which are taught in PCT Patent Application Publication No. WO 96/35469. This PCT application shows a mechanical auger, mechanical abrasion device, heat, a fluid jet, and a rotary toothed blade for mechanical TMR using a percutaneous approach. The mechanical devices described may produce an irregular cut in the myocardium which may result in leaving tissue flaps or fragments in the channel or ventricle. Such debris can be life threatening due to emboli caused by cut tissue.

U.S. patent application Ser. No. 08/713,531, filed on Sep. 13, 1996, and issues on Feb. 16, 1999 as U.S. Pat. No. 5,871,495 teaches of mechanical TMR using cutting devices comprised of inner hollow needles or drill tipped devices mounted within outer hollow needles for TMR. Additionally, a single rotating, hollow needle is described. A sharp cutting blade is used to produce a clean cut.

U.S. patent application Ser. No. 08/773,778, filed on Dec. 26, 1996, now allowed also teaches of a mechanical cutting device used in conjunction with a laser to create drug delivery pockets and/or stimulation zones within a myocardium. The laser is used to introduce the cutting device into the myocardium, and the cutting device defines two, hollow halves that snap together to cut tissue, which is trapped between the halves, to form pockets.

U.S. patent application Ser. No. 08/908,816, filed on Aug. 8, 1997, entitled Method & Apparatus for Myocardial Revascularization and/or Biopsy of the Heart also describes a semi-automatic cardiac tissue removal device for obtaining biopsy samples and/or creating revascularization pathways in the myocardium of the heart, mechanically cuts the pathways using a hand piece with a cutting tip assembly having a hollow needle with an angled, sharpened edge rotatable mounted around a separately advancable stylet.

The stylet defines a piercer to spread the myocardium prior to insertion of the needle and to allow creation of a pathway only within the myocardium. The stylet further defines a plug at the cutting edge of the needle to finish the cutting cleanly and to plug the hollow needle thereby forming a closed chamber for excised tissue.

It is desirable to produce clear, clean revascularization pathways that may be formed only in myocardium, if desired, while ensuring that excised tissue is cleanly removed without leaving tissue flaps and debris behind, using a relatively inexpensive and easily transportable mechanical/laser heart surgical device suitable for heart myocardial revascularization. A design and method that resolves this problem is taught herein for both surgical myocardial revascularization and PTMR procedures.

Moreover, it would be desirable to optionally include a laser vaporization device in such a mechanical coring device with a way for in-situ vaporization of cored tissue which obviates a procedural step of device retrieval from a patient to remove cored tissue from the device distal section.

SUMMARY OF INVENTION

Broadly, an advantage of the present invention is to provide an apparatus and method for mechanically excising myocardial tissue from the heart to produce myocardial revascularization pathways and biopsy samples.

More specifically, an advantage of the present invention is to provide an apparatus and method for mechanically performing myocardial revascularization by cleanly cutting pathways and by using an ancillary laser delivery device that vaporizes cored tissue to prevent debris and/or remaining tissue flaps which may cause emboli or other complications.

Yet another advantage of the present invention is to provide a mechanical cardiac tissue removal device with a tissue coring feature by creating pathways into the myocardium with a rotating hypotube, the hypotube cleanly cuts and secures excised tissue.

Still one more advantage of the present invention is to provide a powered mechanical cardiac tissue removal device configured for single handed use to create pathways in myocardium. The invention provides i) mechanical tissue excision without collateral tissue damage surrounding these pathways and ii) cored tissue debris removal at the device's distal section by laser vaporization.

Yet one more advantage of the present invention is to provide of a mechanical cardiac tissue removal device which retains excised myocardial tissue for subsequent biopsy analysis.

An additional advantage of the present invention is to provide a mechanical cardiac tissue removal device which enables creation of revascularization pathways solely within the myocardium.

The present invention comprises a method and device for mechanically performing cardiac tissue biopsy and/or mechanical myocardial revascularization with a preferred laser components for cored tissue vaporization. Myocardial revascularization is herein defined to include creating revascularization channels within or extending entirely through the myocardium as well as creating stimulation zones in the myocardium which result in revascularization but are not expected to remain completely patent for extended periods. Revascularization channels and/or stimulation zones are herein referred to as pathways.

Although the invention may use various embodiments, several of which are illustrated herein, all require a mechanical cutting tip comprising a hypotube defining a hollow tube for cored tissue retention and subsequent vaporization thereof. The hypotube's distal end defines a cutting edge that cuts a myocardial tissue core as the hypotube is rotated and advanced into the myocardium. The internal structure of the cutting tip preferably includes a necked down portion forming a sharpened step edge that cleanly excises the cored myocardial tissue without leaving tissue flaps or fragments. The excised cored tissue is held by the step edge. Preferably, the central lumen of the hypotube further includes: i) an internal coiled spring section holds the cored tissue in place and/or ii) an optical fiber disposed at the distal end for vaporizing the cored tissue with ancillary aspirating components for withdrawing generated gases.

The operating mechanism for the cutting tip assembly is housed in a hand piece which has an atraumatic tissue contact portion for supporting the cutting tip in location on the heart wall while in operation. In the embodiments shown herein, the contact portion may include one or more suction conduits. Additionally, means for delivering therapeutic substances, such as cardiovascular agents or flushing solutions, to the created pathways may be provided.

Preferably, the cutting tip is removably mounted to the hand piece which defines one or more manual or powered actuators to deploy, rotate, and remove the cutting tip. Alternatively, the device can be used in either i) a minimally invasive surgical (MIS) technique using a modified bronchoscope whose work sleeve includes the coring and cutting distal section forming the hypodermic tubing or ii) a percutaneous transluminal catheter device, both of which can vaporize cored tissue with a laser delivery device contained within the hypotube. The cutting tip optionally may be heated to provide thermal damage to the heart muscle during the creation of the pathway.

In its simplest aspect, suction is not used, therapeutic conduits are not provided, and the cutting tip is not heated. The cutting tip need not be removable in this aspect and the depth stop mechanism may be designed for a maximum depth only.

These and other objects, advantages of the present invention will be apparent to those skilled in the art from the following detailed description with accompanying drawings.

DETAILED DESCRIPTION

Figure 1A:
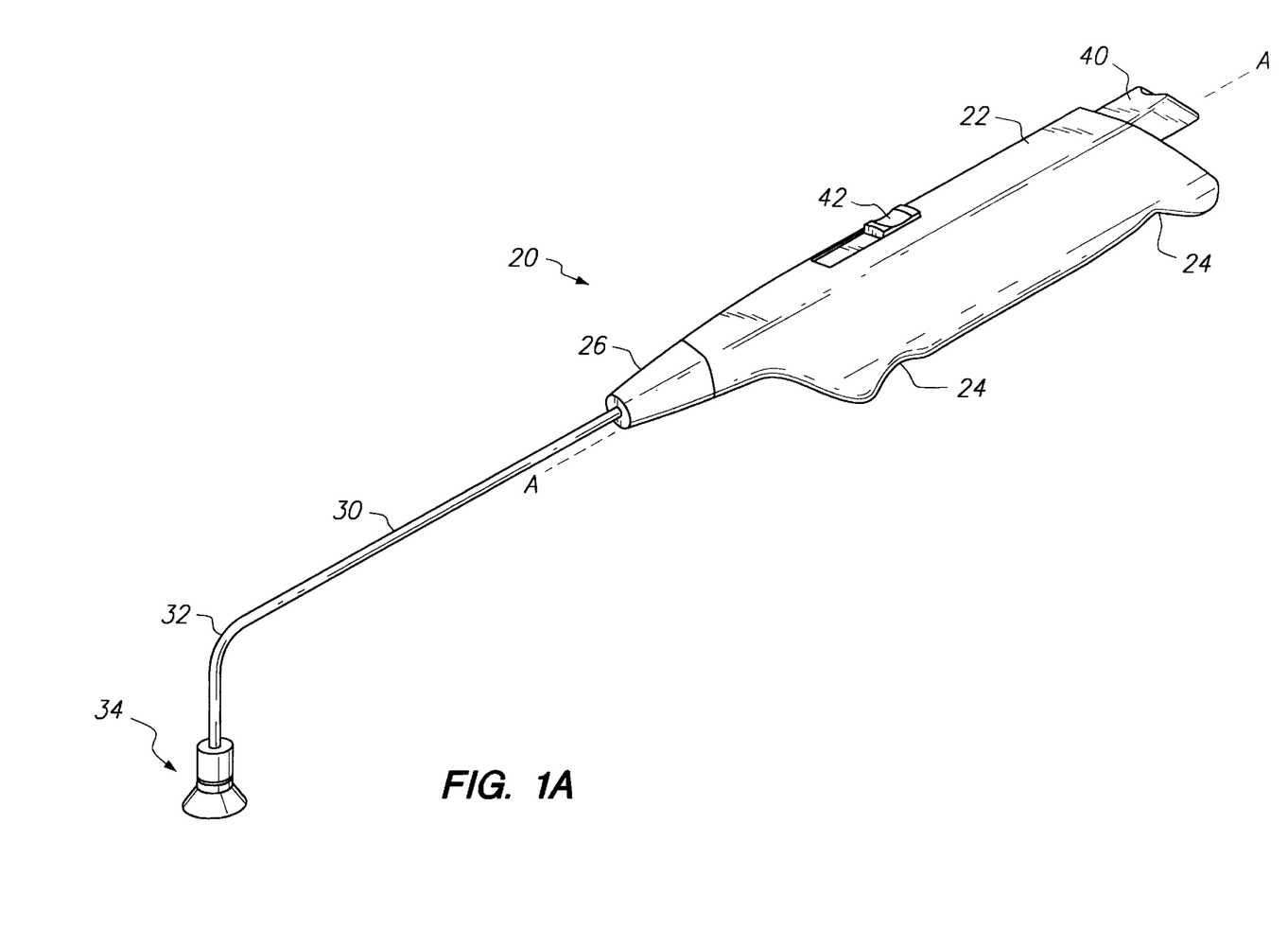
FIG. 1a, similarly shown in U.S. patent application Ser. No. 08/908,816, is a perspective view of a surgical mechanical cardiac tissue removal device showing the atraumatic tissue contact portion and showing alternative single handed grasping positions which may be used to operate the device.

While several embodiments of the invention herein are disclosed, a preferred embodiment of a mechanical cardiac tissue removal device suitable for myocardial revascularization is shown generally in FIG. 1a as reference number 20. This device is similarly shown and described in U.S. patent application Ser. No. 08/908,816, filed on Aug. 8, 1997, entitled Method & Apparatus for Myocardial Revascularization and/or Biopsy of the Heart. The invention described herein is compatible with the embodiments shown for the hand device 20, but does not include the stylet member with attendant drive components that are used for tissue retraction. Moreover, the distal section of the present cutting tip assembly is suitable for a PTMR procedure where the semi-rigid guide member can be replaced with a catheter structure.

As similarly taught in U.S. patent application Ser. No. 08/908,816, the cardiac tissue removal device 20 is particularly suitable for surgical or minimally invasive (MIS) myocardial revascularization and may be held in the hand in several positions, for single handed, left or right hand, operation. See FIG. 1a. As defined herein, a pathway means a revascularization channel which extends into myocardium, may or may not communicate with the ventricle, and a stimulation zone or channel which results in revascularization but is not expected to remain completely patent for extended periods. The semi-automatic device 20 perforates the epicardium of the heart, places the hypotube within the myocardium, rotates and advances the hypotube, and captures the excised tissue within the device for complete removal or vaporization, as described in detail below.

Figure 1B:
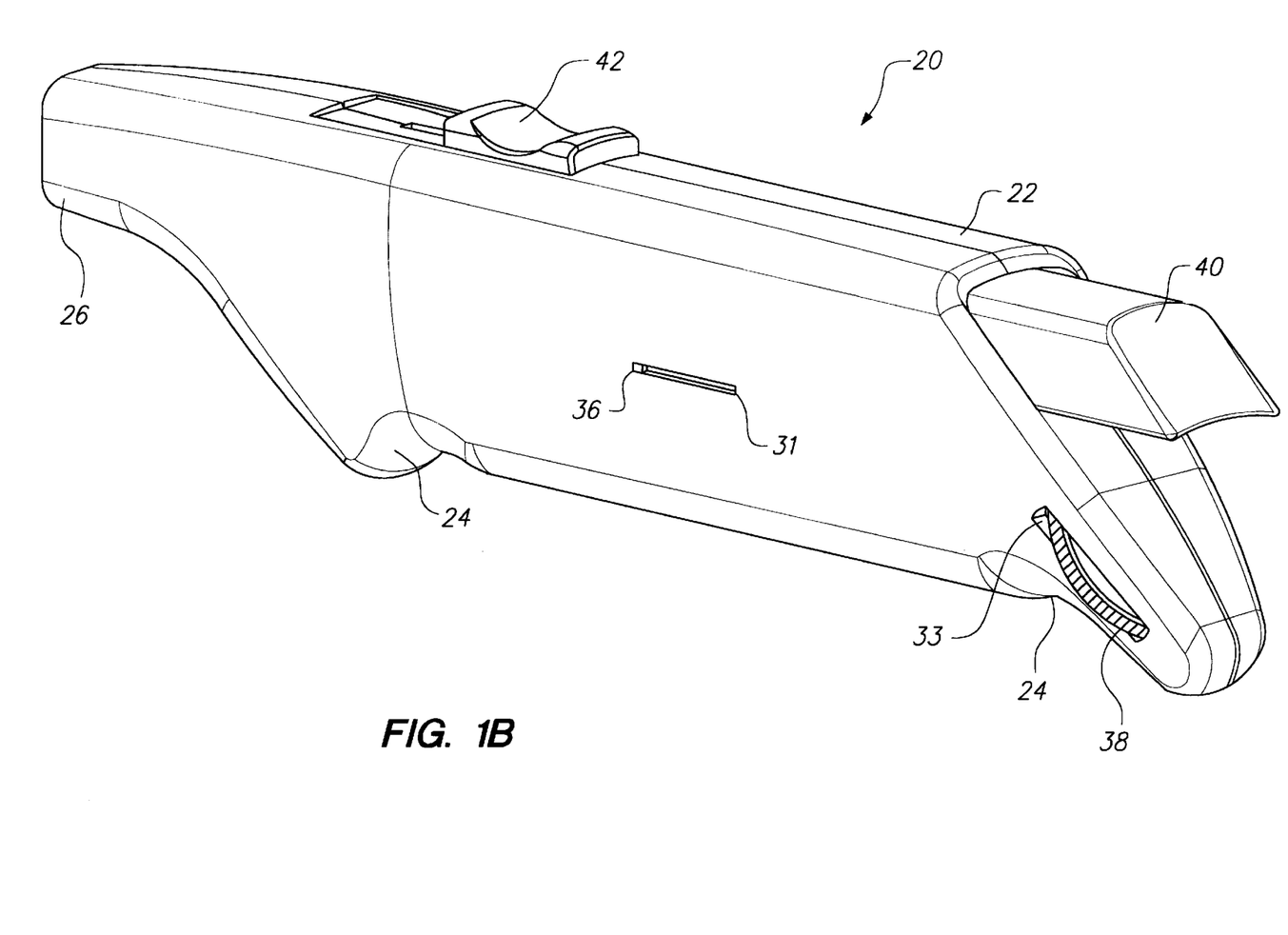
FIG. 1b is a rear side of FIG. 1a in a perspective view of the proximal portion of the device's hand piece showing the depth control actuator and gauge.
Figure 1C:
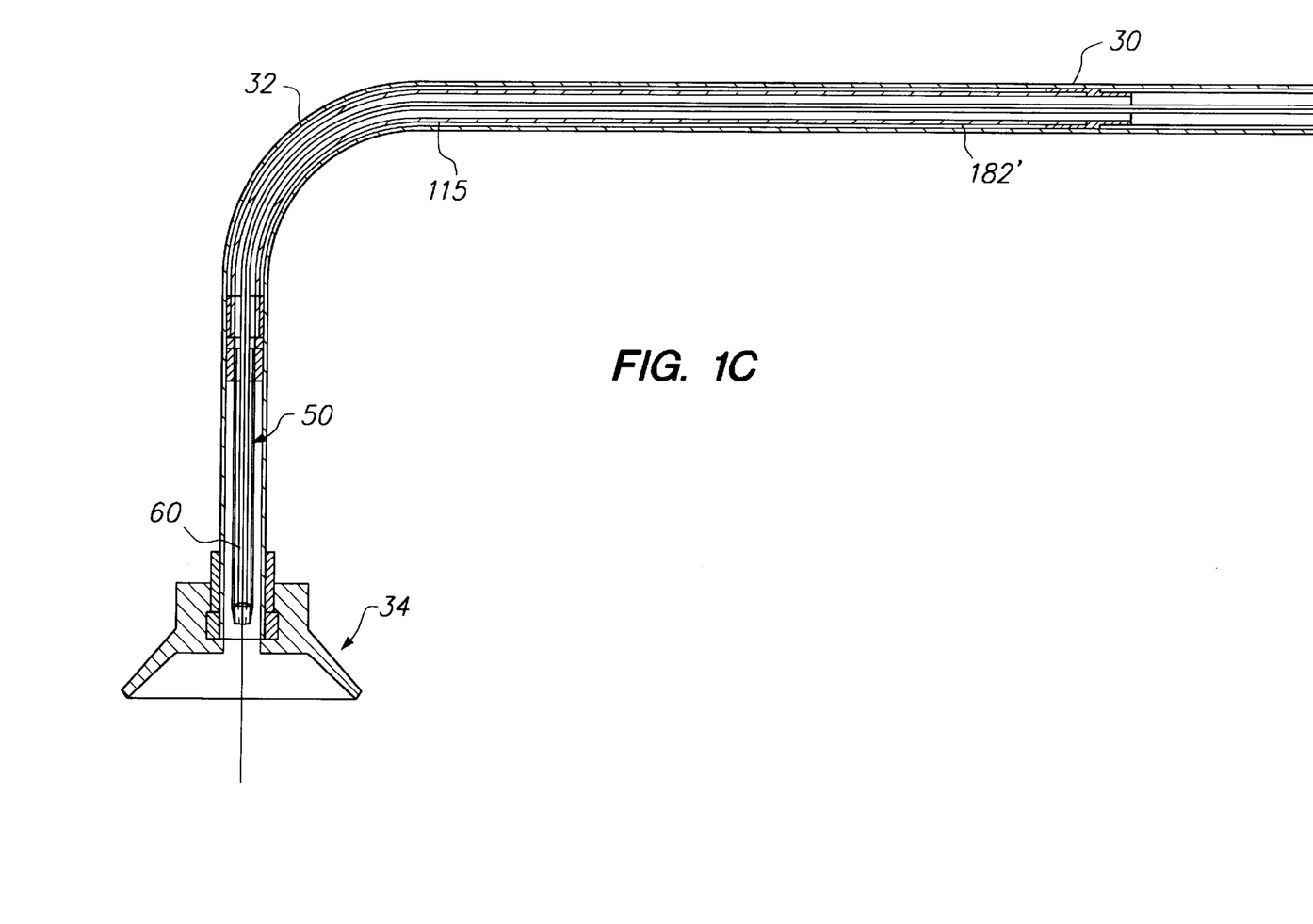
FIG. 1c is a side sectional view of the torquable shaft portion of the mechanical cardiac tissue removal device.

Referring now to FIGS. 1a, 1b & 1c, the preferred mechanical cardiac tissue, removal device 20 includes a housing, handle or hand piece 22 which is a housing molded or machined from a plastic material. The hand piece 22 defines a contoured surface with one or more finger grip indentations 24 which provide tactile feedback of the hand position on the device 22 so the physician need not look away from an ongoing procedure. The contoured surface with indentations 24 further assists the user to securely hold the hand piece without slippage in at least two, different positions during either left or right handed operation of the device 20. A tapered neck portion 26 extends from the hand piece 22 and may be a unitary portion of the hand piece 22, or may be separately molded, as shown, and attached to the hand piece 22. A shaft 30 extends outwardly from the neck portion 26.

Figure 8:
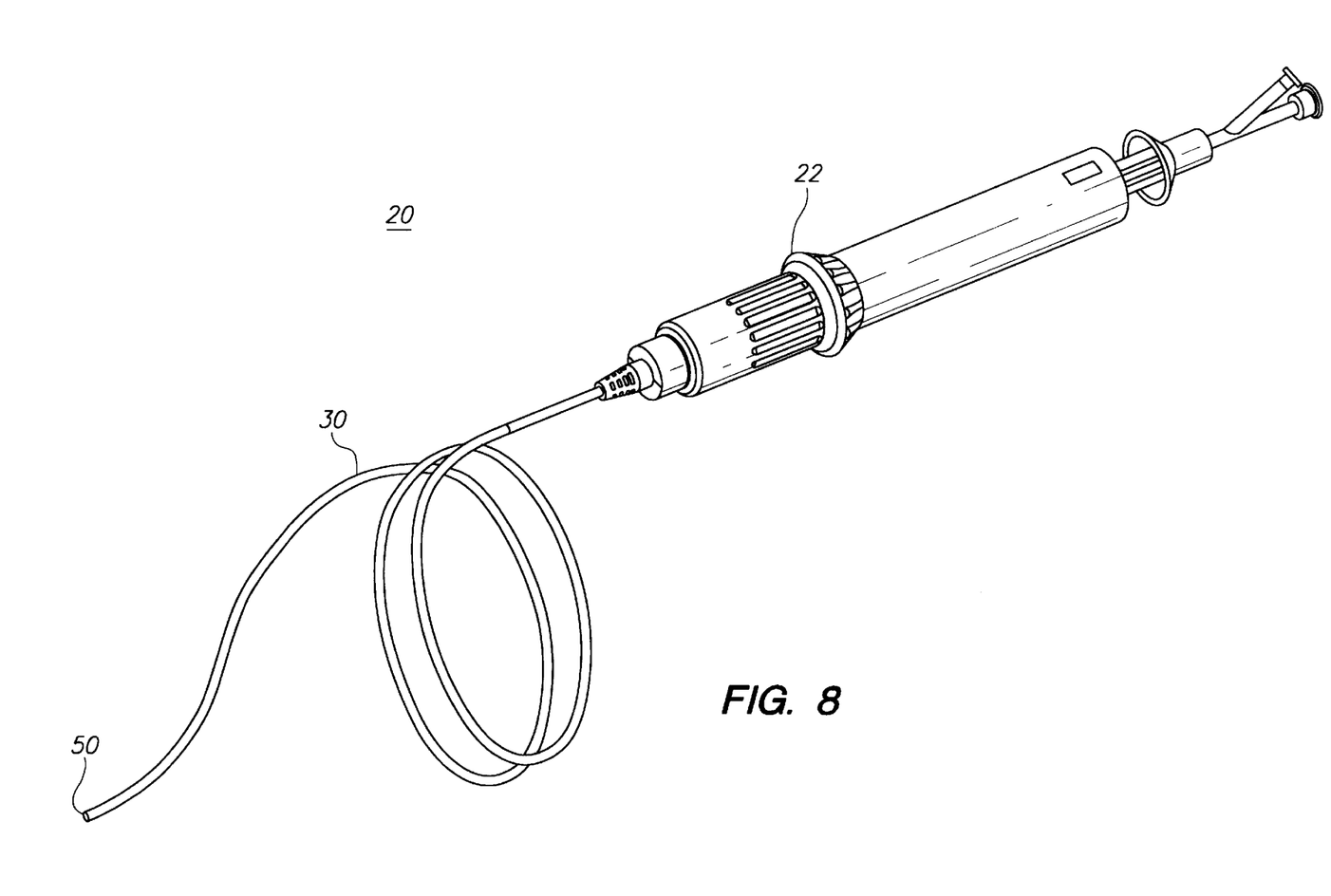
FIG. 8 is a perspective view of the device adapted for percutaneous use.

Alternatively as discussed above, this shaft 30 can be a flexible work sleeve or catheter for use in either a MIS-TMR or PTMR procedure respectively. A MIS-TMR hand device is taught in U.S. patent application Ser. No. 08/94,733 issued on Feb. 22, 2000 as U.S. Pat. No. 6,027,497 entitled "Minimally Invasive Method For Forming Revascularization Channels" which is hereby incorporated by reference. A PTMR system and procedure is taught in U.S. patent application Ser. No. 08/833,352 entitled "Steerable Catheter" filed Apr. 3, 1997, and issued on Mar. 2, 1999 as U.S. Pat. No. 5,876,373 which is hereby incorporated by reference. The PTMR procedure uses a percutaneous steerable laser delivery catheter whose distal tip is positioned near the heart's endocardium for PTMR treatment. A PTMR device and procedure for its use is also taught in U.S. patent application Ser. No. 09/156,963 entitled "Steerable Catheter with Tip Alignment and Surface Contact Detector", and in U.S. patent application Ser. No. 09/156,964 entitled "Drug delivery Catheter with Tip Alignment" both filed Sep. 18, 1998, which are both hereby incorporated by reference. The steerable percutaneous device maintains alignment automatically during tip deflection. The device in S.N. '963 includes a system for detection of interior body wall contact. See FIG. 8.

In an embodiment as similarly taught in U.S. patent application Ser. No. 08/908,816, the shaft 30 may be constructed of metal, plastic or composite materials and may be malleable to allow some ability to change the angle of orientation from axis A. As shown, the torquable shaft 30 defines a generally J-shaped bend 32 and terminates in a protective tip 34. When the neck portion 26 is separately constructed, it may be made rotatable in which case the orientation of the bend 32 and the tip 34 may be altered. Suitable rotation mechanisms include conventional spring fingers, detents, and ratchet assemblies, such as the ratchet mechanism 28 shown in FIG. 2, allowing 360° rotation of the tapered nose 26. As an alternative to a curved shaft, the shaft 30 also may be straight if desired. A conventional articulating joint may also be included for changing the angle of orientation of the tip portion, particularly when inserting and using the device through a port in a minimally invasive surgical procedure.

The protective tip 34 preferably is generally ball, cup or disc shaped and is designed to contact the heart and maintain contact of the device 20 on the heart during formation of a pathway and/or the taking of a biopsy sample. The protective tip 34 may be constructed from generally yieldable materials such as silicone, soft elastic, rubber or foam and may also be metallic or plastic. The protective tip 34 distributes contact forces on the heart, particularly during beating heart myocardial revascularization, and may be permanently attached to the shaft 30 or may be detachable with conventional snap-mount or screw mount mechanisms. Different detachable tips 34, such as suction and drug delivery tips, may be provided to accommodate size and access interests. The tissue contact surface of the protective tip 34 may be textured to provide a gripping surface, and suction may be provided at the proximal end of the hand piece to extend through the shaft 30 to further secure the protective tip 34 to the heart.

Figure 9:
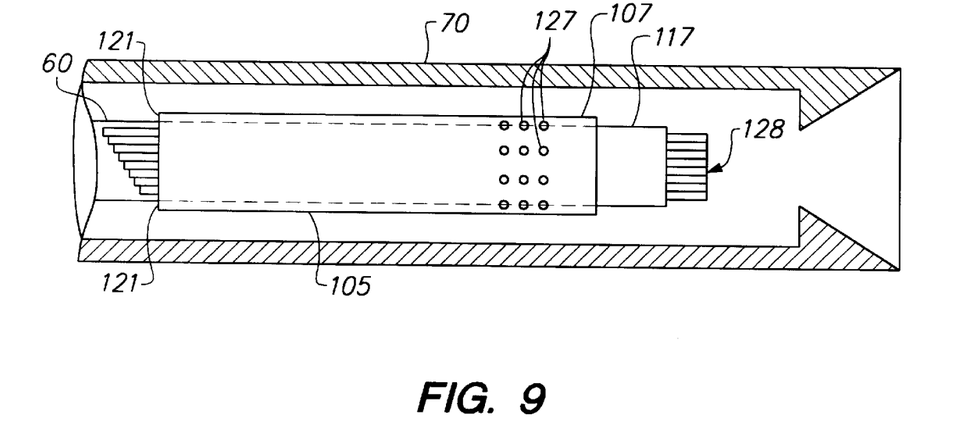
FIG. 9 is a side view of the extendable distal portion of the device adapted for drug delivery.

FIG. 9 is a side view of the extendable portion of the distal end of the device adapted for drug delivery. The vaporization mechanism, a laser device 60 as shown, is disposed within a drug conduit 105. The distal end 107 of the drug conduit 105 has a plurality, one or more, perforations or openings 127 formed through the wall of the drug conduit 105 to allow drugs or other therapeutic agents in space 121 to flow or otherwise be transmitted through drug conduit 105. The distal end 128 of the laser delivery device 60 preferably extends past the distal end 107 of the drug conduit 105. The laser delivery device 116 may consist of a single or bundle of individual optical fibers. An outer jacket 117 surrounds the fiber optic and thus the combination of the outer jacket 117 and drug conduit 105 defines an interstitial drug channel 121 through which drugs can be conveyed through conduit 105 and out the plurality of perforations 127. It will understood that the outer jacket 117 is optional and may be omitted. In such a case, utilizing a single fiber mounted within conduit 105 will result in drug delivery from the plurality of perforations 127 in essentially the same manner as described above. However, in the case of a bundle of fibers without an outer jacket 117, drug solution or other substances will flow around each of the individual fibers of the bundle, thus resulting in percolation of drug out of the drug conduit 105 at either or both of the plurality of perforations 127 and the distal end of the fiber bundle. In the embodiment shown, individual perforations 127 are spaced about outer jacket 117. It will be understood that more or fewer perforations may be used, and perforations located at various axial positions located adjacent the distal end 107 of the drug conduit 105. Alternattively, a drug conduit may be disposed within the fiber bundle or the bundle may include a space between fibers for introduction of drugs (not shown).

One or more operator buttons or other conventional finger actuated mechanisms extend through the hand piece 22 to operate the cardiac tissue removal device 20. A push button 40 extends out of the proximal end of the hand piece 22 to operate the device in a semi-automatic manner as described below. A second sliding button 42 is operatively connected to the push button 40 thereby allowing operation of the device to be controlled from various hand positions. In addition to buttons 40, 42, a depth gauge 36 preferably is provided on the side of the hand piece, and the selection of desired pathway depth is controlled by thumb wheel 38 extending through hand piece slot 33 shown in FIG. 1b. The depth gauge 36 is a sliding knob which protrudes through a slot 31 in the hand piece. Depth markings are provided and may be matched with the position of the slidable knob. Selection of optimum depth for pathways depends upon a number of factors, including but not limited to the depth of the myocardium and the desired depth of the pathway. Generally, the depth stop selector should allow selection of depths between about 0.5–3.5 mm, and selection of a maximum depth of about 2.0–2.5 mm would avoid communication of a surgically created pathway with the heart's ventricle, or perforation of the epicardium in a PTMR procedure. Channel communication with the ventricle is undesirable in some cases. For instance, a non-communicating myocardial pocket treated with angiogenic drugs is such an example.

Determination of the depth of the heart wall may be done conventionally prior to performing a myocardial revascularization procedure, or the depth may be determined dynamically during the myocardial revascularization procedure using ultrasound as described in U.S. patent application Ser. No. 08/852,977, filed May 6, 1997, and issued on Feb. 15, 2000 as U.S. Pat. No. 6,024,703 and which are incorporated by reference herein. The sensor may be coupled to the distal end of the device, preferably attached to the distal end of the shaft or the stabilization device, where applicable.

Figure 2:
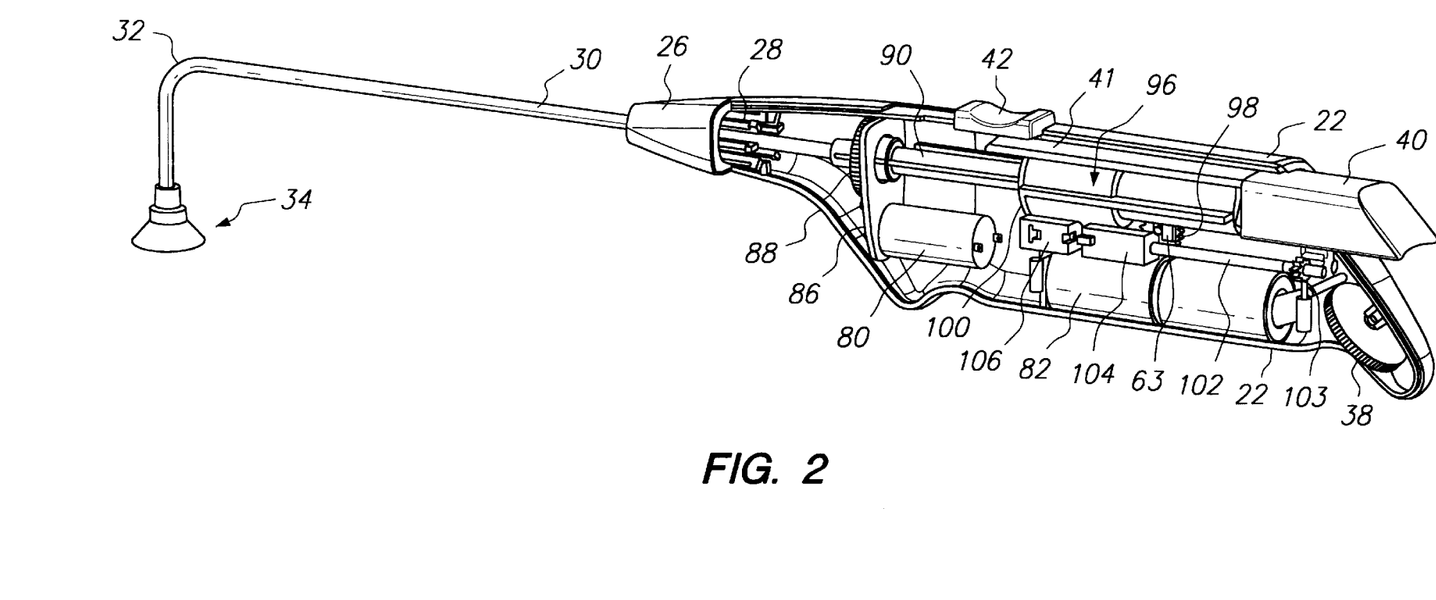
FIG. 2 is a side view taken of the hand device.
Figure 3:
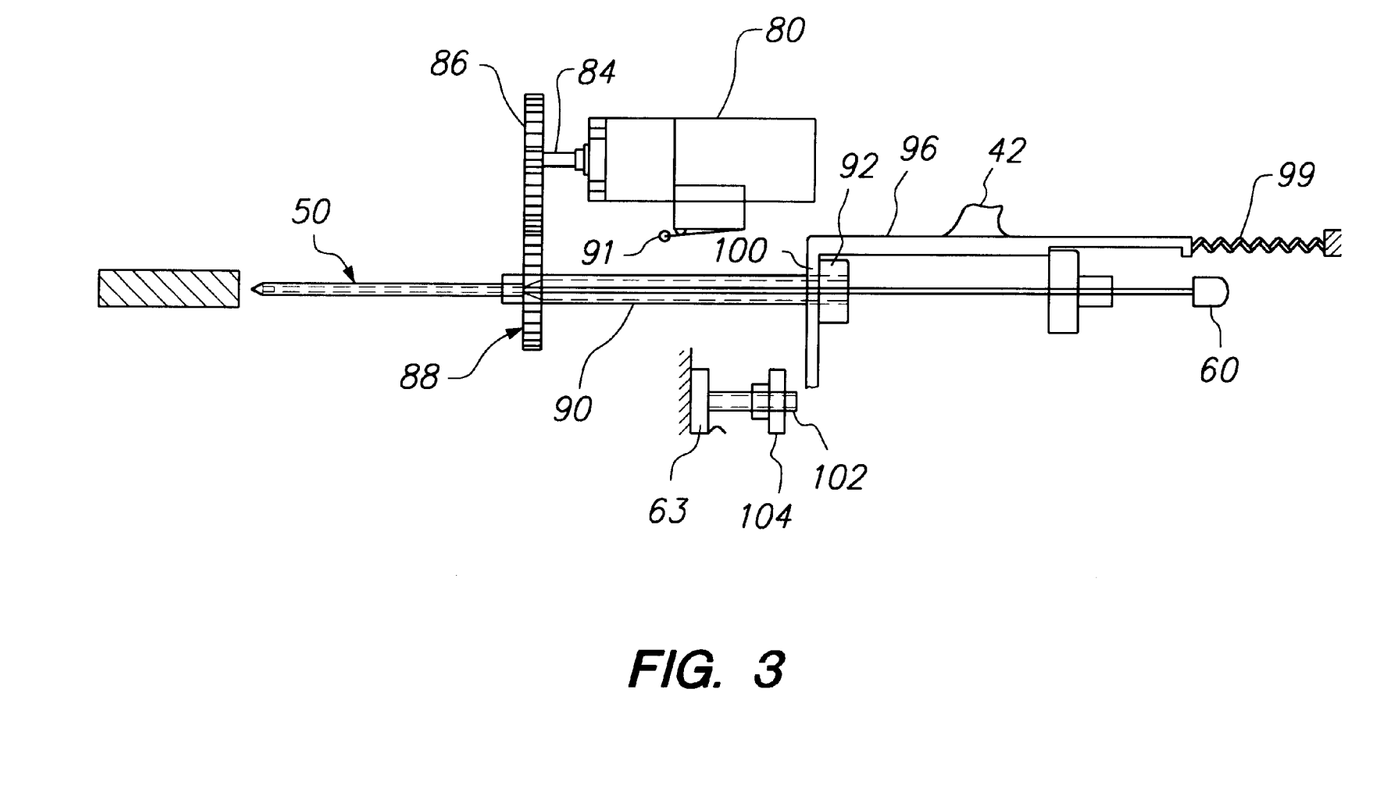
FIG. 3 is a mechanical schematic view of the major components and their relationship within the device.

FIG. 2 shows the major components for controlling the cutting tip 50 of the cardiac tissue removal device 20, and FIG. 3 shows such components diagrammatically to illustrate the operating relationships between the components.

Figure 4A:
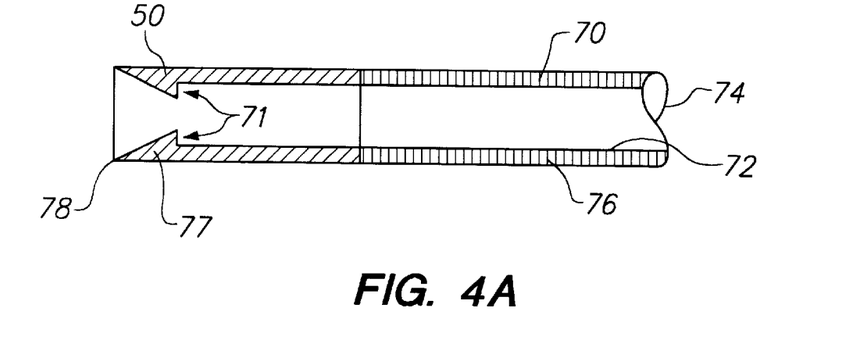
FIGS. 4a, 4b & 4c are enlarged views of the distal end of a preferred cutting tip showing the cutting edge with step edge, a retaining spring and laser fiber in the hypotube respectively.
Figure 4B:
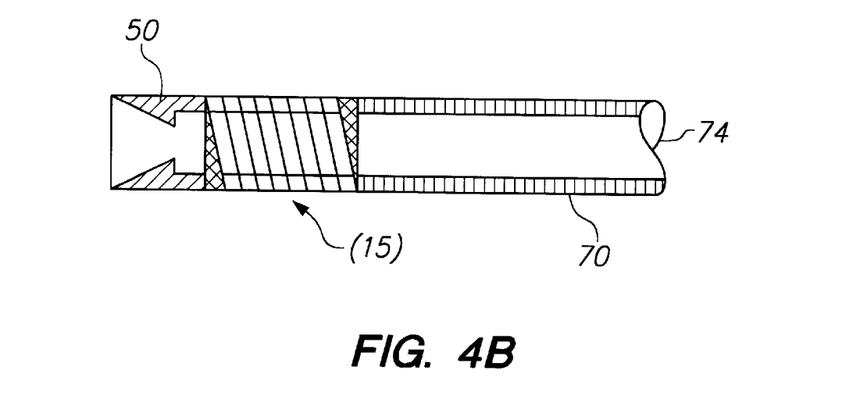
Figure 4C:
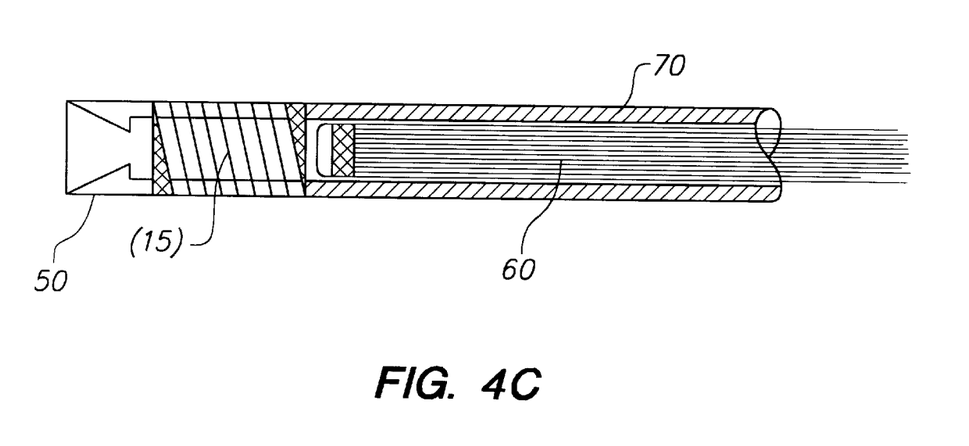
Figure 5A:
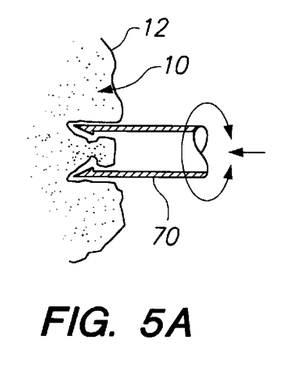
FIGS. 5a, 5b & 5c are sequential views of the cutting tip entering and exiting tissue to create a pathway or take a tissue sample.
Figure 5B:
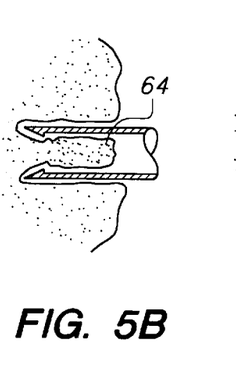
Figure 5C:
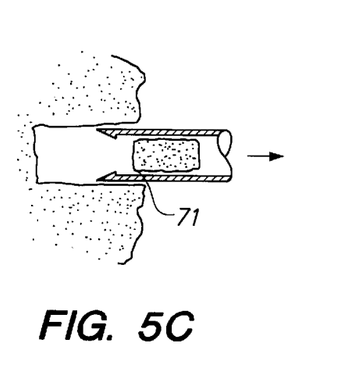
Figure 7A:
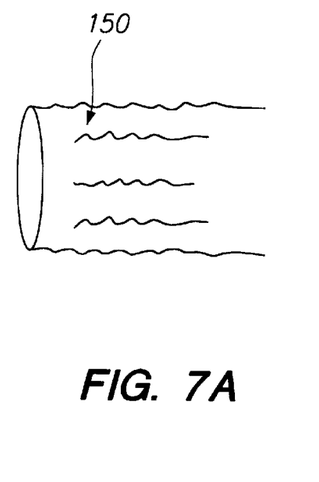
FIG. 7a is a side view of the extendable distal portion of the device wherein the external surface is textured.
Figure 7B:
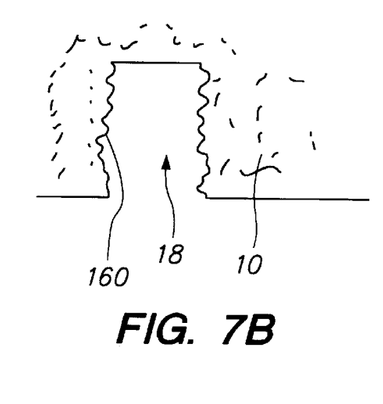
FIG. 7b is a view of the increased injury surface area with the use of externally textured extendable distal portion of the device.

Referring now to FIGS. 4a, 4b & 4c, following selection of a depth for a desired pathway, a cutting tip 50 shown in FIG. 3 may be slidably extended through the shaft 30 and out of the protective tip 34 by pressing push button 40 or 42 as shown in FIG. 1c. The preferred components of the cutting tip 50 comprise an optical fiber 60 mounted within a catheter, for example a hollow hypotube 70. The proximal portion of the distal tip of the catheter is preferably flexible, and may be constructed of, for example, a coiled wire spring, braided tubing or a combination thereof to create different stiffness zones and flexibility's depending on the envisioned usage of the device, surgical or percutaneous. Preferably the cutting tip is of a rigid, partially rigid or substantially rigid material. The distal portion of the distal tip of the catheter is a cutting edge. The distal tip portion of the extendable portion of the device, all or a portion of the cutting tip, may also have a textured external surface 150 (FIG. 7a). Textured as used in the present invention includes but is not limited to surfaces that are abraded, abrasive, serrated, rough, uneven, jagged, craggy or anything that would create an increased surface area of injury 160 in the pathway 18 after excision of the sample or plug when utilizing the device of the present invention (FIG. 7b). The effect would further stimulate angiogenesis. The optical fiber 60 and the hypotube 70 are advanced into the heart tissue to create a pathway. The hollow hypotube 70 is a tapered tube. The hypotube 70 defines an interior wall 72 surrounding a lumen 74 and an exterior wall 76. The inner lumen diameter is approximately 0.5–2.5 mm depending upon the intended diameter of the pathway. The distal end of the hypotube 70 defines a beveled portion 77 which terminates to form a sharp cutting edge 78. Rotation of the hypotube 70, as described below, results in a sharp, clean cut by the beveled portion 77 and edge 78. The beveled portion 77 and the edge 78 allow the rotating hypotube 70 to cut through tissue with minimal axial force.

The beveled portion 77 can include a helical cutting surface to additionally cut tissue as it enters the lumen of the hypotube. An optional step edge 71 retains cored tissue when the hypotube 70 retracts. Alternatively, the hypotube may be a straight tube without the step wherein the laser parts off the tissue. A spring 15 shown in FIGS. 4b & 4c may also be in the distal tip section for additional tissue retention capability. The spring 15 imparts added flexibility to the distal tip section and which is preferred for percutaneous use of the device. In FIG. 4b, the coil spring 15 is in the internal lumen with open spacing between the spring turns so that rotating the hypotube 70 clockwise winds the tissue coring sample inward similarly to that of flutes on a drill.

The optical fiber 60 is either statically mounted within the hypotube 70 or catheter or allowed to translate if the design desires variability to the distal tip of the optical fiber 60. Referring now to FIG. 1c, the catheter cutting tip is advanced through the shaped portion 32 of the shaft 30 using a torquable, bendable shaft insert 115. The torquable insert 115 is a coiled wire spring 182, or wire mesh proximal tubing portion, located near the distal end of the cutting tip to provide flexibility to allow the cutting tip to follow the bend 32 in the shaft 30. Such a design is required for a flexible catheter when used in a PTMR catheter design. The torquable shaft insert 115 also may be constructed from a super elastic or shape memory material. For example materials such as nitinol are desirable for enhanced percentage of elongation and/or super elastic properties. Phase transition metals undergo changes in their elasticity with changes in temperature. One such group of materials are nickel titanium alloys known as nitinol, whose use in vascular medical products in well known in the art. Upon heating above a fixed temperature, the austenite temperature, the elasticity of the nitinol increase significantly. The alloy of nitinol used can be engineered to have an austenite temperature within a selected range which be in the area of body temperature (e.g. 37 C.) or higher.

Beginning with activation by the user of either button 40 or 42, linear movement of the non-actuated button occurs because the two buttons 40, 42 are connected by a shaft 41. The shaft 41 is a generally L shaped bar which is connected to the primary operating component of the device 20 by a connecting bar 96. The connecting bar 96 is the primary movable component which causes movement and operation of other components, including the cutting tip 50. The connecting bar 96 is a generally tubular structure defining flanges and slots designed to control movement of the hypotube 70 with the optional optical fiber 60 within. Axially extending flanges secure positional alignment of the connecting bar 96 to the housing 22 by being slidably engaged in housing slots. When the connecting bar 96 moves axially towards the distal end of the device 20, the hypotube 70 is pushed along with the bar. A hypotube stop 63 prevents further advancement of the hypotube 70 with optional optical fiber 60 relative to the connecting bar 96 when the stop 63 contacts a portion of the flange 100. Also, axle 90 is then pushed forward when connecting bar 96 comes into contact with flange 92 which connects to flange 100. Stop 63 contacts flange 100 to stop movement of axle 90. The connecting bar 96 further defines an axle stop 100 which limits axial travel of an axle 90. A return spring 99 is attached between the connecting bar 96 and the device's housing, or to the button 40, to bias the connecting bar 96 in its most proximal position when force is released from button 40 or 42.

Maximum travel distances into tissue by the hypotube 70 and the optical fiber 60 are controlled by the travel of the connecting bar 96 as controlled by the operator using a depth setting mechanism which extends through the housing to a depth adjustment assembly comprising, for example, an adjustment screw 102 and nut 104, as shown in FIGS. 2 & 3. Movement of the thumb wheel 38 which is attached to a pulley or gear mechanism 103 with an O-ring, causes the gear mechanism, which is attached to the threaded portion of screw 102, to rotate the adjustment screw 102 to change the position of the nut 104 which serves as a stop for the hypotube 70 or catheter advancement. The position of the nut 104 is adjusted relative to a stop 63. Alternative depth stop mechanisms may be used that include a ratchet or cammed mechanism or discrete stops.

The semi-automatic operation is provided by a small motor 80, for example a Micro-Mo 6 Volt DC motor, powered by a battery 82, such as a Duracell™ 2/3A Li/MnO2 battery, or may have an air, fluid, or other known actuation mechanism to cause rotation. Operation of the motor 80 causes rotation of an armature shaft 84 which terminates in a drive gear mechanism having 1 or more gears such as spur gears 86, 88. Gear 88 attaches, and is preferably keyed, to an axle 90. Rotation of the gears 86, 88 transmits torque and rotational movement in a clockwise or counter-clockwise direction to the hollow axle 90 which defines a proximal flange 92 and houses the cutting tip 50. Activation of the motor 80 occurs only when electrical contact is made between the connecting bar 96 and a contact plate of the motor 80 to complete a circuit between the motor 80 and batteries 82. Alternatively, a contact switch 91 may be used and is tripped as shown in FIG. 3 when contacted by a connecting bar 96.

Figure 6A:
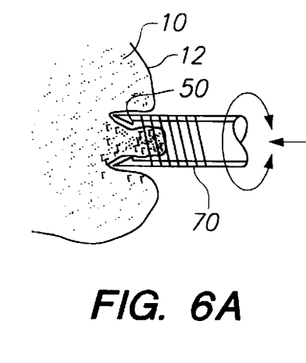
FIGS. 6a, 6b, 6c & 6d are sequential views of the cutting tip entering and exiting tissue to create a pathway with subsequent tissue vaporization.
Figure 6B:
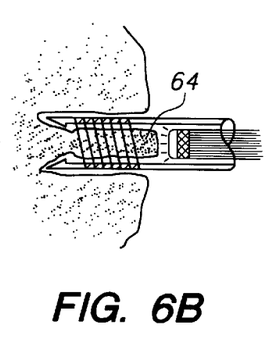
Figure 6C:
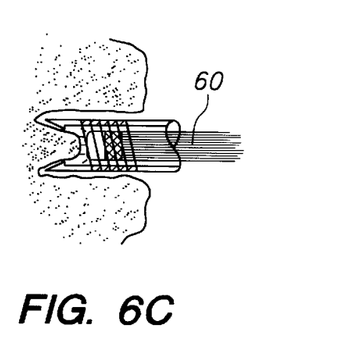

Operation of the cardiac tissue removal device 20 to form a pathway is best shown in FIGS. 6a–6c. In FIG. 6a, the coring tip 50 is shown positioned entering a wall of the heart, in this case, the epicardium 12, prior to initiating pathway formation. The hypotube 70 is positioned over and around the plug 64. The initiation of pathway formation by pushing button 40 or 42 as shown in FIG. 1 to insert the cutting tip 50 through the epicardium 12 to allow entry of the distal end of the hypotube 70 through the epicardium 12 with minimal trauma thereto. Placement of the cutting tip 50 within myocardium, cuts the tissue to form a pathway, continued pressing of button 40, 42 vaporizes the cut tissue.

FIG. 6b shows advancement and rotation of the hypotube 70 to its maximum depth by continued depression of push button 40 so the connecting bar 96 with attached flange 100 engages the adjusting nut 104 stopping the hypotube 70 advancement. As the hypotube 70 rotates and advances, the excised, cut or severed tissue plug 64 is urged by bevel 78, parted off, severed, cleaved, slashed, dissected, sliced, weakened and separated, ripped, tugged or torn off or even simply removed as it expands across cutting edge 71 to expand into lumen 74 where it is held by the step 71 until the hypotube 70 reaches its maximum depth, as shown in FIG. 6b when the flange 100 contacts the adjusting nut 104. At maximum depth, rotating edge 78 of the hypotube and cutting edge 71 together produce a clean finishing cut to complete a pathway. Alternatively, at maximum depth, the cutting edge 71 both cuts and retains the excised to complete a pathway upon withdrawal of the device and to retain the cut tissue for laser fiber advancement and ablation. The excised tissue, including any trimmed tissue captured within the hypotube 70 is held within the hypotube's on step edge 71. Upon removal of the cardiac tissue from the pathway using optical fiber 60, as shown in FIG. 6c, the excised tissue 64 is completely removed revealing a pathway 18 formed completely within the myocardium 10. The pierced, spread opening through the epicardium 12 closes. Release of the push button 40 causes the biasing return spring 99 to retract the connecting bar. The motor 80 shuts off when the connecting bar 96 clears the micro switch 94 and the components return to the initial starting positions at the end of the retraction cycle. Alternatively, the cutting tip 50 may be retracted by reversing the direction of travel of the buttons 40, 42.

Figure 6D:
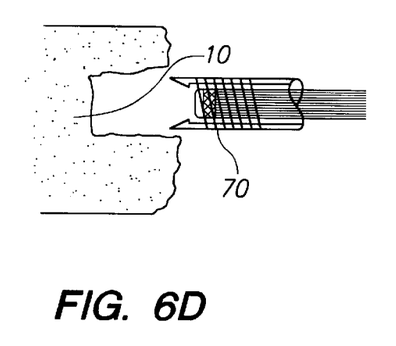

Operation of the cardiac tissue removal device 20 to form a pathway with tissue vaporization is shown in FIGS. 6a–6d. In a similar manner, the cutting tip 50 performs the same operation as discussed above in FIGS. 6a and 6b. After attaining a required pathway depth, the vaporization mechanism, for example but not limited to a laser fiber or a bundle of laser fibers 60 irradiates previously cored tissue causing the vaporization thereof. The device 20 may include aspirating components to withdraw gases in the hypotube 70. The aspiration components would be coupled to or in communication with the lumen of the catheter and could for example be connected to a vacuum mechanism or may comprise a syringe. Alternatively, a flushing mechanism may be employed to remove gases. Saline could be used to displace the gases in the catheter or hypotube. Aspiration of gases would follow the retraction or removal of the tissue vaporization device from the lumen. However, if a flushing mechanism is employed this may not be necessary. The hypotube 70 is then retracted as shown in FIG. 6d from the pathway and the procedure is repeated.

Figure 6E:
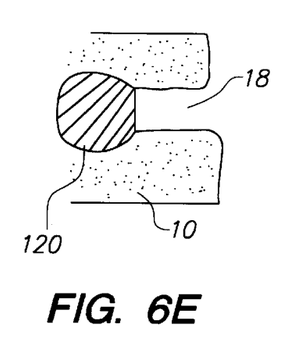
FIG. 6e is a view of the creation of thermal injury in the remaining tissue.

The creation of viable pathways using the cutting tip assemblies may by performed by first heating the cutting tip to a temperature of at least 60 degrees Celsius. This provides thermal damage 120, as depicted in FIG. 6e, to the remaining tissue or heart wall 10, in addition to the thermal damage created from frictional engagement of the cutting tip. The use of heat simulates the thermal shock of the prior art laser methods. A separate heating element(not shown), such as a conventional thermal band(not shown) may be provided to ensure that each cutting tip is heated. Alternatively, a plurality of detachable optical fibers may be heated in an oven or heating block(not shown) and attached with a snap lock or quick disconnect mechanism to the hand piece.

Referring again to FIGS. 4a–4c, the torquable shaft portion may be extended the length of the cutting tip to create a flexible assembly for insertion through a catheter to form pathways from the inside of the heart's left ventricle. In such an embodiment, a catheter is inserted conventionally through the vascular, perhaps through the femoral artery, into the ventricle using a conventional guidewire procedure. Following catheter positioning within the ventricle, the guidewire is removed and the torquable cutting tip 50 is introduced through the catheter to the heart's endocardium to create pathways. Control of the cutting tip 50 at the catheter's distal end is by an external hand-piece device having comparable components as described above for a surgical TMR hand-piece unit 20, particularly the depth control mechanism to ensure that a pathway does not penetrate the heart's outer epicardium.

The term tissue and muscle are used interchangeably in the present invention and disclosure and include any body mass or foreign body mass capable of being cored, excised, severed, partially severed, substantially severed, dislodged, weakened, weakened and torn, entrapped or cut, retained and optionally vaporized with the disclosed apparatus.

The term drug or drugs as used in the present invention and disclosure herein includes any and all drugs and therapeutic agents for use or useable within in or on the body including, but not limited to gene therapies, angiogenic agents, anti-arrhythmic agents, growth factors, etc. U.S. patent application Ser. No. 09/156,963 entitled "Drug Delivery Catheter with Tip Alignment", and U.S. patent application Ser. No. 08/773,872 filed Dec. 12, 1996 and issued on Jul. 20, 1999 as U.S. Pat. No. 5,925,012 entitled "Laser Assisted Drug Delivery" teach drugs or therapeutic agents, delivery formulations as well dosages useful in the practice of this invention and are hereby incorporated by reference in their entirety. Additionally included are those therapeutic agents known now or in the future to those skilled in the art.

The vaporization mechanism includes but is not limited to energy delivery devices, such as fiber optics, individual fibers or fiber bundles, as well as radio frequency and thermal tissue ablation devices. For the purpose of this disclosure it is understood that the term vaporization mechanism will also include devices known and used in medicine and other disciplines today and in the future for destroying the excised tissue retained in the catheter. Preferably the excised tissue is destroyed prior to removing the device from the body, more preferably before removal of the device from the excision site, to avoid the loss of any excised tissue debris into the body.

Any medical laser is useful in the practice of the present invention. The Holmium, YAG or excimer lasers are particularly suited for use in the present invention. However, any suitable laser source, could provide laser energy to the laser delivery device for performing the disclosed methods.

As will be understood by those familiar with the art, the present invention may be embodied in other specific forms without departing from the spirit or essential characteristics thereof. The motor may be configured to require operator activation instead of being automatically tripped, and suction may be used for removal of excised tissue from the hypotube lumen. The housing may be made of materials other than plastic and may be configured differently to provide alternative designs.

What is claimed is:

1. An apparatus for cutting a pathway in tissue comprising: a housing, a catheter coupled to the housing, the catheter including a lumen and proximal and distal portions, an end effector at the distal portion of the catheter for cutting a pathway in the tissue, a tissue vaporization device in combination with the distal portion of the catheter so that the tissue severed by the end effector and held within the distal end of the catheter is vaporized by the tissue vaporization device in the distal end of the catheter in the body.

2. The apparatus of claim 1 further including a therapeutic agent delivery device in combination with the tissue vaporization device for delivering one or more therapeutic agents to the pathway.

3. The apparatus of claim 1 further including a therapeutic agent delivery device within the lumen of the catheter for delivering one or more therapeutic agents to the pathway.

4. The apparatus of claim 1 further including a shaft having a lumen and proximal and distal portions, the shaft housing the catheter, the catheter translatable in the shaft and extendable out the distal portion of the shaft.

5. The apparatus of claim 4 further including at the distal portion of the shaft a device for stabilizing the end effector in contact with the tissue.

6. The apparatus of claim 4 further including a sensing device at the distal portion of the shaft for determining the depth of the tissue.

7. The apparatus of claim 1 further including a rotation mechanism coupled to the housing and causing rotation of the catheter.

8. The apparatus of claim 1 wherein the effector end is removably mounted to the housing.

9. The apparatus of claim 1 further including a depth stop mechanism coupled to the housing for controlling advancement of the effector end.

10. The apparatus of claim 1 further including an element for heating the effector end coupled to the distal portion of the catheter and to an energy source.

11. The apparatus of claim 1 wherein the tissue vaporization device comprises a laser energy delivery device translatable within the lumen of the catheter.

12. The apparatus of claim 1 wherein the tissue vaporization device comprises a laser energy delivery device mounted within the lumen of the catheter and coupled to a laser energy source.

13. The apparatus of claim 1 further including a gas removal mechanism in communication with the lumen of the catheter for withdrawing generated gases created during vaporization.

14. A tissue removal apparatus for use in a body comprising:
    a coring mechanism having a lumen for excised tissue, and
    a tissue vaporization mechanism housed within the lumen of the coring mechanism for destroying excised tissue within the coring mechanism in the body.

15. The apparatus of claim 14 wherein the tissue vaporization mechanism is translatable within the lumen of the coring mechanism.

16. The apparatus of claim 14 wherein the coring mechanism comprises a catheter having proximal and distal ends, the distal end of the catheter comprising a cutting portion.

17. The apparatus of claim 14 wherein the coring mechanism comprises a hypotube having proximal and distal ends, the distal end of the hypotube comprising a cutting portion.

18. The apparatus of claim 16 wherein the cutting portion is substantially rigid.

19. The apparatus of claim 16 wherein the cutting portion is rigid.

20. The apparatus of claim 16 wherein the cutting portion comprises a cutting edge having proximal and distal ends.

21. The apparatus of claim 20 wherein the cutting portion further includes a step edge to retain excised tissue.

22. The apparatus of claim 16 comprising a flexibility imparting device at the distal end of the catheter adjacent the proximal end of the cutting portion.

23. The apparatus of claim 21 wherein the flexibility imparting device is a spring.

24. The apparatus of claim 16 wherein the cutting portion further comprises an external textured surface to create a pathway with a jagged surface.

25. The apparatus of claim 23 wherein the external textured surface is serrated.

26. The apparatus of claim 16 wherein the proximal end of the catheter is flexible.

27. The apparatus of claim 16 wherein the proximal end of the catheter is substantially flexible.

28. The apparatus of claim 16 wherein at least a portion of the catheter is flexible.

29. The apparatus of claim 16 wherein the catheter is torquable.

30. The apparatus of claim 16 wherein the catheter further comprises a torquable insert element in combination with the catheter.

31. The apparatus of claim 30 wherein the torquable insert is embedded in the wall of the catheter.

32. The apparatus of claim 30 wherein the torquable insert comprises a spring.

33. The apparatus of claim 30 wherein the torquable insert comprises wire mesh tubing.

34. The apparatus of claim 14 wherein the tissue vaporization mechanism comprises a laser energy delivery device having proximal and distal ends.

35. The apparatus of claim 34 wherein the laser energy the laser energy delivery device is one or more optical fibers.

36. The apparatus of claim 35 further including a therapeutic agent delivery device at the distal portion of the laser delivery device.

37. The apparatus of claim 16 further including a hand piece coupled to the proximal end of the catheter.

38. The apparatus of claim 16 further including a motor mechanism operatively coupled to the catheter, for motion of the distal end of the catheter.

39. The apparatus of claim 38 further including a depth stop mechanism coupled to the hand piece for controlling advancement of the catheter.

40. The apparatus of claim 16 further including a sensing device at the distal end of the catheter for determining the depth of the tissue.

41. The apparatus of claim 16 further including a shaft with a lumen having distal and proximal ends, the catheter translatable within the lumen of the shaft.

42. The apparatus of claim 41 further including a stabilization device at the distal end of the shaft for stabilizing the coring mechanism in contact with the tissue.

43. The apparatus of claim 42 wherein the stabilization device is one or more suction conduits.

44. A method for excising tissue in a body comprising:
  a) providing an apparatus comprising: a mechanical tissue excision mechanism housing a tissue vaporization mechanism;
  b) placing the distal portion of the apparatus on a tissue surface;
  c) creating a pathway in the tissue and capturing excised tissue within the distal portion of the apparatus; and
  d) vaporizing the excised tissue within the apparatus.

45. The method of claim 44 wherein step c) further includes delivery of at least one therapeutic agent to the pathway.

46. The method of claim 44 subsequent to step c) delivering at least one therapeutic agent to the pathway.

47. The method of claim 44 subsequent step d) delivering at least one therapeutic agent to the pathway.

48. The method of claim 44 wherein the tissue surface in step b) is the epicardium.

49. The method of claim 44 wherein the tissue surface in step b) is the endocardium.

50. The method of claim 44 wherein step c) further includes causing thermal injury to a remaining tissue.

51. The method of claim 44 wherein step c) includes advancement and rotation of the mechanical tissue excision mechanism in the tissue.

52. The method of claim 44 wherein step d) includes firing the tissue vaporization mechanism within the mechanical tissue excision mechanism.

53. The method of claim 44 the apparatus further including a gas removal mechanism in combination with the tissue vaporization mechanism and step e) comprising removing gases from the tissue vaporization mechanism.

54. A method for enhancing trauma while creating a myocardial pathway comprising
  a) providing a mechanical tissue coring device having a textured external distal surface,
  b) advancing the tissue coring device into myocardial tissue
  c) removing a cored tissue sample while providing an increased trauma surface area within the pathway.

55. A method for creating a revascularization pathway in a body tissue comprising:
  a) providing an apparatus comprising: a mechanical tissue coring mechanism housing a tissue vaporization mechanism;
  b) placing the distal portion of the apparatus on a tissue surface;
  c) coring a pathway in the tissue; and
  d) vaporizing the cored tissue within the apparatus.

56. The apparatus of claim 1 wherein the tissue vaporization device comprises a radio frequency ablation device.

57. The apparatus of claim 14 wherein the tissue vaporization device comprises a radio frequency ablation device.

* * * * *

UNITED STATES PATENT AND TRADEMARK OFFICE
CERTIFICATE OF CORRECTION

PATENT NO. : 6,162,214
DATED : December 19, 2000
INVENTOR(S) : Richard L. Mueller and Alexander Khairkhahan It is certified that error appears in the above-identified patent and that said Letters Patent is hereby corrected as shown below:

Title page,
Item [54], delete "CORNING" and add -- CORING --;

Column 1,
Line 1, delete "CORNING" and add -- CORING --;

Signed and Sealed this

Sixteenth Day of October, 2001

Attest:

NICHOLAS P. GODICI
Acting Director of the United States Patent and Trademark Office Attesting Officer